United States Patent
Britva et al.

(10) Patent No.: US 11,045,249 B2
(45) Date of Patent: Jun. 29, 2021

(54) ELECTRODE FOR A SYSTEM FOR HEATING BIOLOGICAL TISSUE VIA RF ENERGY

(71) Applicant: Alma Lasers Ltd., Caesarea (IL)

(72) Inventors: Alexander Britva, Migdal Ha'Emek (IL); Alexander Dverin, Netanya (IL); Ziv Karni, Kfar Shmaryahu (IL)

(73) Assignee: Alma Lasers

( * ) Notice: Subject to any disclaimer, the term of this patent is extended or adjusted under 35 U.S.C. 154(b) by 20 days.

(21) Appl. No.: 14/446,594

(22) Filed: Jul. 30, 2014

(65) Prior Publication Data
US 2015/0045857 A1    Feb. 12, 2015

(30) Foreign Application Priority Data
Aug. 6, 2013 (GB) ...................................... 1314019

(51) Int. Cl.
| | |
|---|---|
| A61N 1/04 | (2006.01) |
| A61B 18/14 | (2006.01) |
| A61N 1/40 | (2006.01) |
| A61B 18/00 | (2006.01) |
| A61N 5/10 | (2006.01) |

(52) U.S. Cl.
CPC ............ *A61B 18/14* (2013.01); *A61N 1/0476* (2013.01); *A61N 1/403* (2013.01); *A61B 2018/00023* (2013.01); *A61B 2018/00208* (2013.01); *A61B 2018/00452* (2013.01); *A61B 2018/147* (2013.01); *A61N 2005/1005* (2013.01)

(58) Field of Classification Search
CPC .................. A61B 2018/147; A61B 2018/1417
See application file for complete search history.

(56) References Cited

U.S. PATENT DOCUMENTS

| | | | |
|---|---|---|---|
| 5,052,997 A | 10/1991 | Ruggera | |
| 5,101,836 A * | 4/1992 | Lee | ........................... A61N 5/04 |
| | | | 607/155 |
| 5,919,219 A * | 7/1999 | Knowlton | .............. A61B 18/12 |
| | | | 606/33 |

(Continued)

FOREIGN PATENT DOCUMENTS

| | | |
|---|---|---|
| EP | 1715810 | 5/2012 |
| WO | 20091126117 | 11/2012 |

OTHER PUBLICATIONS

Combined Search and Examination Report in United Kingdom patent application GB1314019.9, which is the foreign priority filing for this application.

(Continued)

*Primary Examiner* — Luther Behringer
(74) *Attorney, Agent, or Firm* — Richard Jaffe; Clifford D. Hyra

(57) ABSTRACT

An electrode is disclosed for use in a system for heating biological tissue via RF energy. The electrode comprises a plurality of electrically conductive pins projecting from, and in electrical contact with, an electrically conductive common base. The base is connectible to a source of RF energy and the spaced ends of the pins remote from the base have contact regions for introducing RF energy from the source into the biological tissue. Each contact region is sufficiently small to achieve uniform dielectric heating in the biological tissue beneath the contact region at the frequency of the applied RF energy.

15 Claims, 4 Drawing Sheets

(56) References Cited

U.S. PATENT DOCUMENTS

| | | | |
|---|---|---|---|
| 8,321,031 B1 | 11/2012 | Ellman et al. | |
| 9,283,029 B2 * | 3/2016 | Britva | A61B 18/042 |
| 2004/0030332 A1 * | 2/2004 | Knowlton | A61N 1/30 |
| | | | 606/41 |
| 2005/0065510 A1 * | 3/2005 | Carmel | A61B 18/148 |
| | | | 606/41 |
| 2007/0106349 A1 * | 5/2007 | Karni | A61B 18/042 |
| | | | 607/101 |
| 2008/0183167 A1 * | 7/2008 | Britva | A61B 18/042 |
| | | | 606/41 |
| 2008/0183252 A1 * | 7/2008 | Khen | A61B 18/14 |
| | | | 607/101 |
| 2009/0254155 A1 * | 10/2009 | Kanarsky | A61N 5/0613 |
| | | | 607/89 |
| 2011/0009783 A1 * | 1/2011 | Dverin | A61B 18/14 |
| | | | 601/137 |
| 2013/0245727 A1 * | 9/2013 | Kothare | A61N 1/328 |
| | | | 607/102 |
| 2015/0133906 A1 * | 5/2015 | Horton | A61B 18/12 |
| | | | 606/28 |

OTHER PUBLICATIONS

"Skin effect," Wikipedia, https://en.wikipedia.org/wiki/Skin_effect, accessed Jun. 1, 2020 "Skin Depth Equation Formula (aka Skin Effect)—RF Cafe", RF Cafe, https://www.rfcafe.com/references/electrical/skin-depth.htm, accessed Jun. 2, 2020

\* cited by examiner

ELECTRODE FOR A SYSTEM FOR HEATING BIOLOGICAL TISSUE VIA RF ENERGY

CROSS REFERENCE TO RELATED APPLICATIONS

This application claims priority under 35 USC § 119 to UK patent application no. GB1314019.9, filed Aug. 6, 2013, entitled "Electrode for a System for Heating Biological Tissue via RF Energy", which is incorporated herein by reference in its entirety.

BACKGROUND OF THE INVENTION

The present invention relates to a system for heating biological tissue via RF energy.

EP 1715810 discloses a system for heating biological tissue which uses an electrode to apply RF energy to the tissue. The system described in the latter patent includes an applicator, forming a single electrode of the system, which comprises a dielectric barrier, contactable with a surface of a biological tissue to be heated. The applicator is capable of delivering a desired amount of energy to a predetermined energy dissipation zone beneath the surface of the biological tissue, the selected target being positioned within the predetermined energy dissipation zone. An RF energy source produces an output RF power signal directed to the single applicator, the RF being radiatively or capacitively coupled by the applicator into the biological tissue. A phase changer is provided which is controllable to vary the phase of the output RF power signal so that energy from it is concentrated primarily in the predetermined energy dissipation zone, which lies at a phase dependent depth beneath the surface of the biological tissue. An impedance matching network serves to match an impedance characteristic of the RF energy source and the phase shifter to the impedance of the biological tissue belonging to the subject so that the RF power signal may pass through the surface of the biological tissue without undergoing reflection. An RF resonator is located in the applicator which is operative to accumulate and release the desired amount of energy cyclically whereby a significant portion of the energy of the RF signal is concentrated in the predetermined energy dissipation zone.

In operation, the applicator serves to convey the output RF power signal from the RF energy source through the surface of the biological tissue to the predetermined energy dissipation zone after the output has been processed by the phase shifter, the impedance matching network and the resonator. Operation of the system thereby produces a reverse thermal gradient in the biological tissue in that the surface is maintained at a lower temperature than the predetermined energy dissipation zone without using a cooling device for cooling the surface.

The applicator does not connect a ground electrode to the biological tissue and therefore permits free propagation of the waves of the output RF power signal in the energy dissipation zone.

The present invention is particularly concerned with the design of an electrode for use in such a system.

BRIEF SUMMARY OF THE INVENTION

According to the present invention, there is provided an electrode for use in a system for heating biological tissue via RF energy, the electrode comprising a plurality of electrically conductive pins projecting from, and in electrical contact with, an electrically conductive common base, wherein the base is connectible to a source of RF energy and the spaced ends of the pins remote from the base have contact regions for introducing RF energy from the source into the biological tissue, and wherein each contact region is sufficiently small to achieve uniform dielectric heating in the biological tissue beneath the contact region at the frequency of the applied RF energy.

In some embodiments, at least the contact regions of the pins are covered with an electrically insulating material.

In some embodiments of the invention, the electrode is mounted in an applicator incorporating a motor for rotating the electrode.

The electrode may conveniently be water cooled by means of a cooling system mounted within the applicator, which may also house components of the circuit supplying RF energy to the electrode, such as parts of the resonator of the impedance matching circuit.

BRIEF DESCRIPTION OF THE DRAWINGS

The invention will now be described further, by way of example, with reference to the accompanying drawings, in which.

DETAILED DESCRIPTION OF THE INVENTION

The applicator of the invention is intended to be connected to an RF supply circuit which may be constructed as described in EP 1715810. The latter specification is incorporated herein by reference in its entirety to avoid the need to describe the RF supply circuit in detail in the present context. For an understanding of the present description, it suffices to know that the RF energy generated by a source is transmitted to the applicator through a circuit that includes a resonator, a circuit for varying the phase of the RF energy and an impedance matching circuit. There is a single electrode, or applicator, employed without a ground electrode, permitting homogeneous application of RF-energy, which is directed primarily towards rotation, and vibration of dipole molecules, especially water molecules, in the applied electromagnetic wave. In EP 1715810, the size of the contact surface of the single electrode, that is to say the diameter of the flat or convex disc-shaped contact region of the electrode, is limited by the frequency of the RF energy and reduces with increasing frequency for the reasons explained below. The present invention is intended to overcome this limitation by allowing a larger total contact area to be used, capable of applying energy with a power in the range of 100 to 400 Watts at a frequency in the range 30 MHz to 100 MHz.

Figure 1:
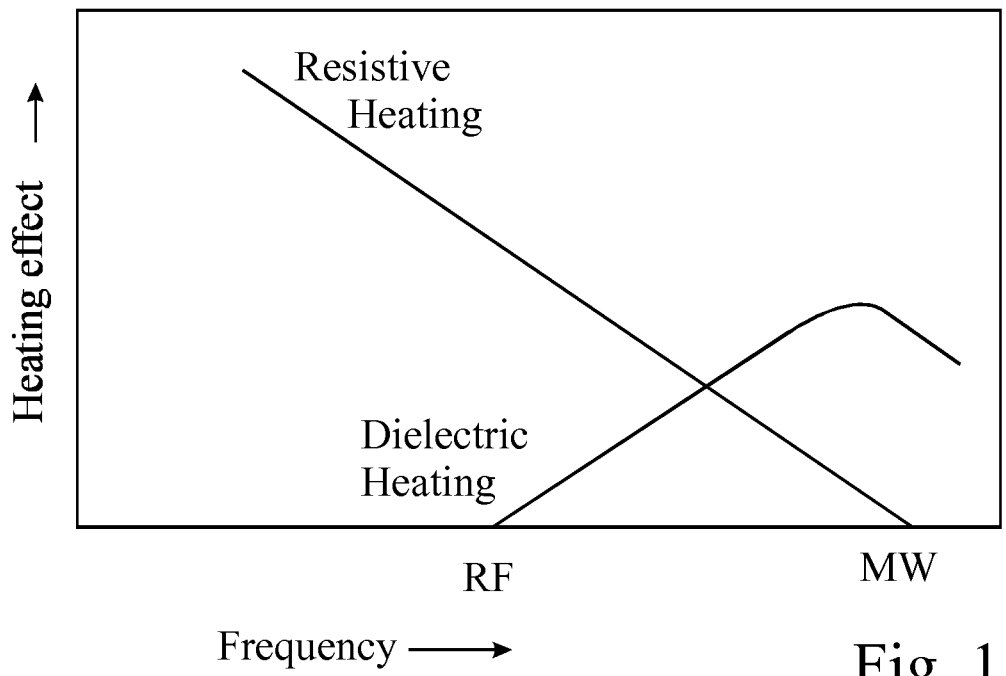
FIG. 1 is a schematic graph showing the manner in which resistive heating and dielectric heating vary with the frequency of the applied RF energy.

Different frequencies rely on different mechanisms to generate heat within the tissue being treated, the variation of the heating effect of these mechanisms with the RF frequency being shown in FIG. 1. At lower frequencies, the heating effect is predominantly resistive and caused by migration of ions. Resistive heating however suffers from certain disadvantages, namely low penetration depth and inhomogeneous heat distribution which varies with the conductivity of the medium being heated.

At higher frequencies, dielectric heating, which is caused by vibration of water dipoles in the alternating fields, becomes the more dominant cause of heating. Because of increased penetration depth and improved homogeneity, higher RF frequencies, in the range of 30 MHz to 100 MHz, are to be preferred. Higher operating frequency, however, can only be applied effectively using smaller diameter electrodes and this limits the RF power that can be applied and increases the time needed to treat a given area of tissue. For efficient and fast treatment it is desirable to use an electrode with a diameter of 4-6 cm but, at an operating frequency of 30 MHz or more, a single electrode of that size would not produce uniform heating, as will now be explained.

High-frequency currents induce magnetic fields that in turn apply a force to the electrons in the high-frequency current itself. These fields drive the moving electrons away from the center of the current flow resulting in the current in a wire being driven towards the surface. The skin depth $\delta$, which is defined as the depth at which the current drops to a value of 37% (1/e) of its value at the surface, at a particular frequency, $\omega$, is given by.

$$\delta = \sqrt{(2\rho/\omega\mu)}$$

where $\rho$ is the resistivity of the material, and $\mu$ is its permeability.

Figure 3:
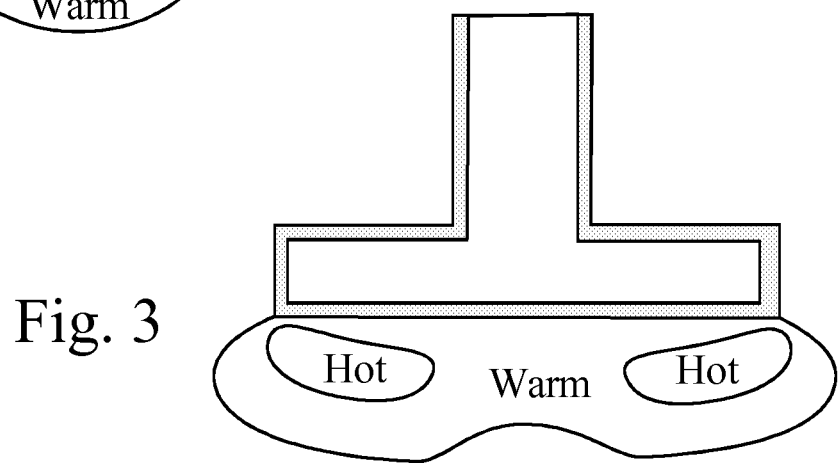
FIG. 3 is a sketch similar to that of FIG. 2 but showing the temperature of biological to assume beneath an electrode having a large contact region.

Therefore the current flow in the electrode for high frequency RF energy is as shown by the shaded area in FIG. 3 of the drawings but the skin depth increases as the frequency drops.

Figure 2:
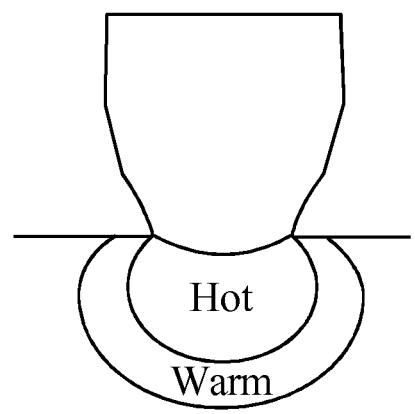
FIG. 2 is a sketch showing the temperature of biological tissue beneath an electrode having a small contact region.

When using a small contact region, as shown in FIG. 2, the heating effect in the tissue is substantially uniform. However, when using electrodes with a larger contact area, as represented in FIG. 3, the coupling of RF-energy begins from the periphery of the applicator and will be lowest at the central axis. If the applicator diameter is more than 3-4 cm at 40 MHz operating frequency, the central zone of the applicator introduces lower RF-energy than the outer part. The intensity of the RF-wave at the outer zone is much higher then at the centre of the applicator electrode and therefore a heating process will be inhomogeneous. The resulting heat distribution, as shown in FIG. 3, is a ring of high temperature around the periphery of the electrode and a cooler area on the axis of the electrode.

To allow treatment of a larger area while still achieving uniform heat distribution, electrodes embodying the invention have several spaced apart contact regions, each of which is sufficiently small to avoid the above effect and achieve uniform heating. However, the combined effect of the spaced contact areas defined by the tips of the pins can be the equivalent of the area of a single electrode having a diameter in excess of 4 cm.

Figure 4:
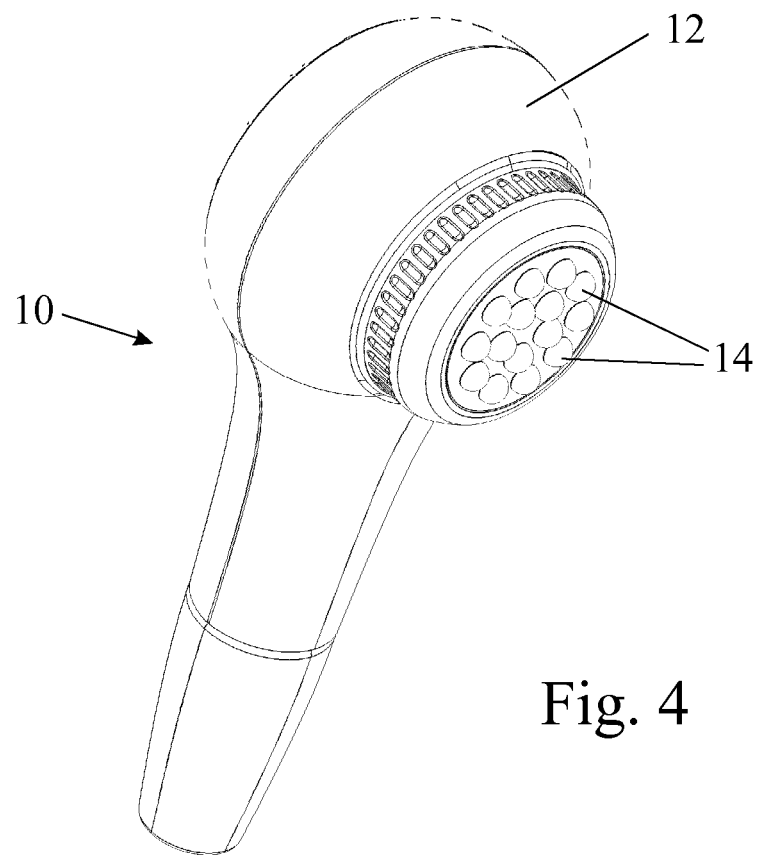
FIG. 4 is a perspective view of an assembled applicator incorporating an electrode of the present invention.

The applicator 10 in FIG. 4 comprises an outer shell 12 of two-part plastics construction and an electrode with multiple spaced contact regions 14. At least the contact regions 14 may have an insulating coating.

Figure 5:
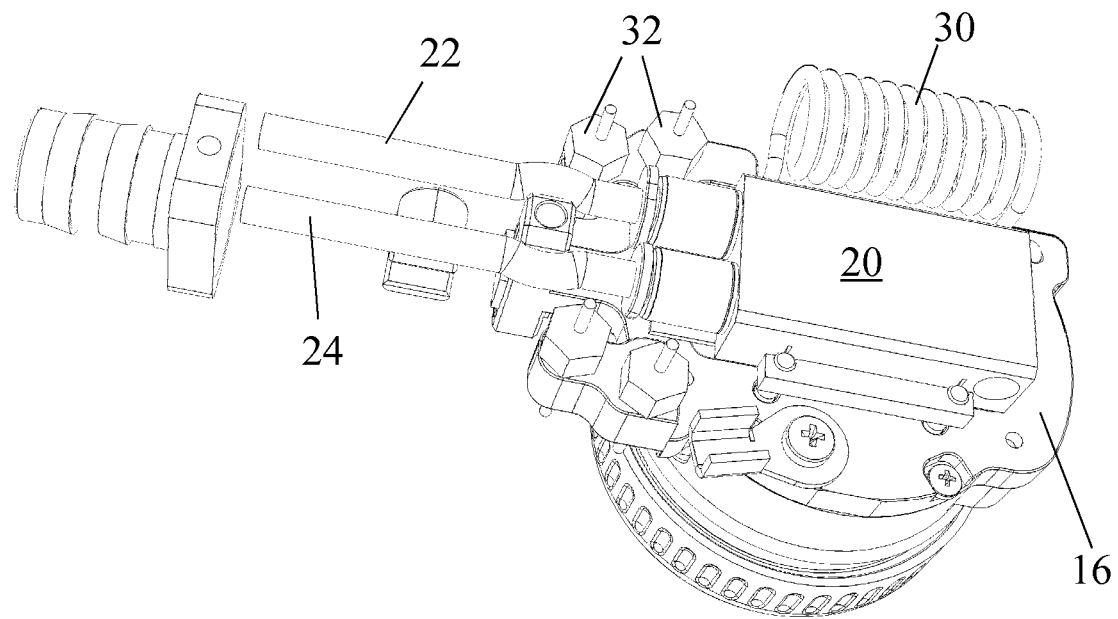
FIG. 5 is a rear perspective view of the applicator of FIG. 4 with the outer housing removed.

As seen in FIG. 5, which shows a rear view of the applicator with the outer shell removed, the applicator 10 houses, in addition to the RF electrode, a water cooling circuit for cooling the electrode. The cooling circuit includes a small tank 20 and supply and return pipes 22, 24 connected to the tank 2. Some electrical components, such as a choke 30 and capacitors 32, of the circuit supplying RF power to the electrode are also housed in the applicator, but these need not be described in detail in the present context, as the invention is mainly concerned with the construction of the electrode.

Figure 6:
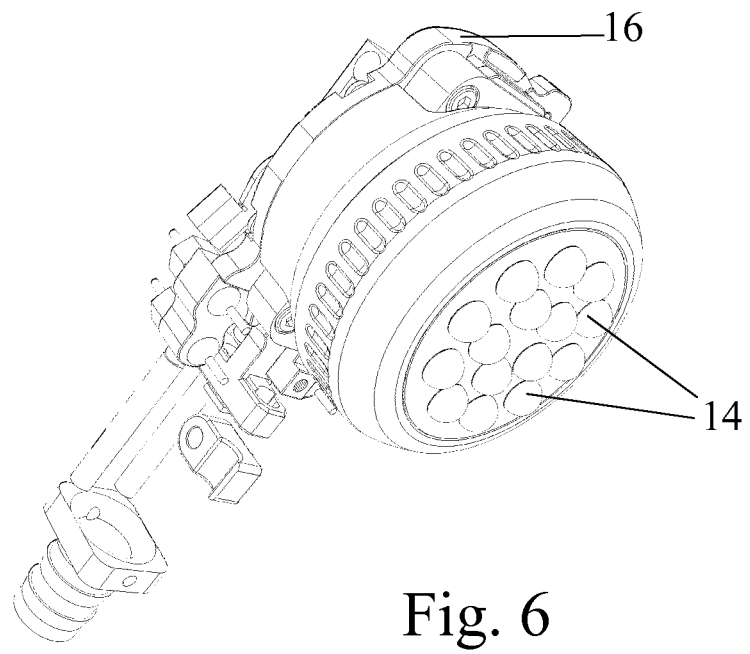
FIG. 6 is front perspective of the applicator in FIG. 4 with some of the housing removed.
Figure 7:
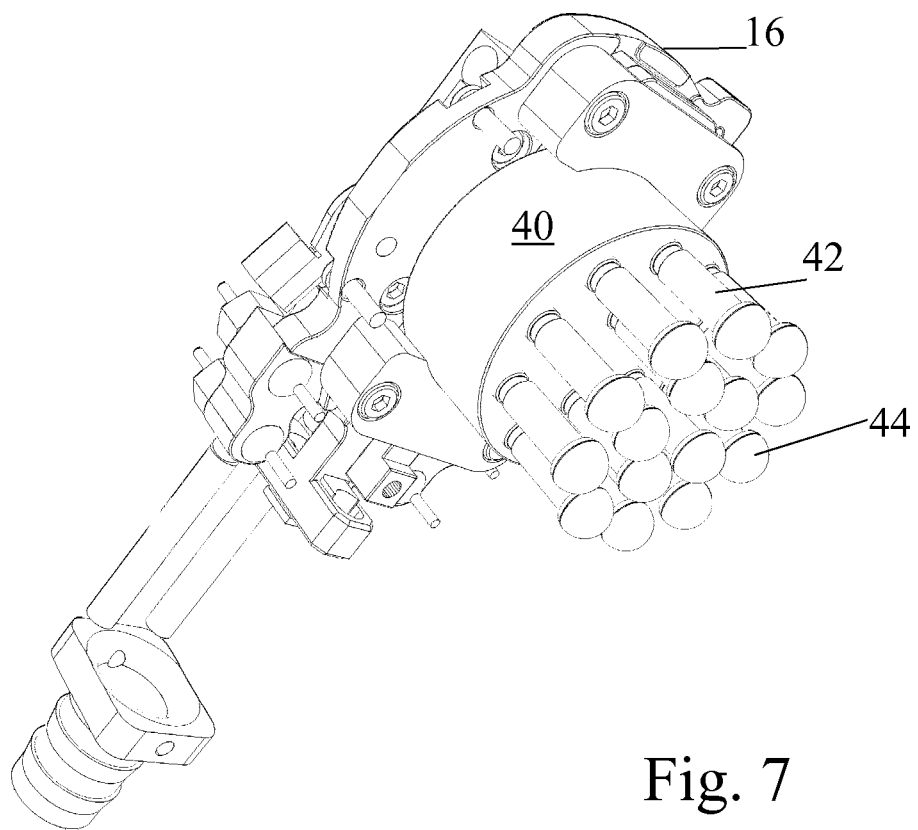
FIG. 7 is a front perspective view similar to that of FIG. 6 but with some components removed to expose the electrode.
Figure 8:
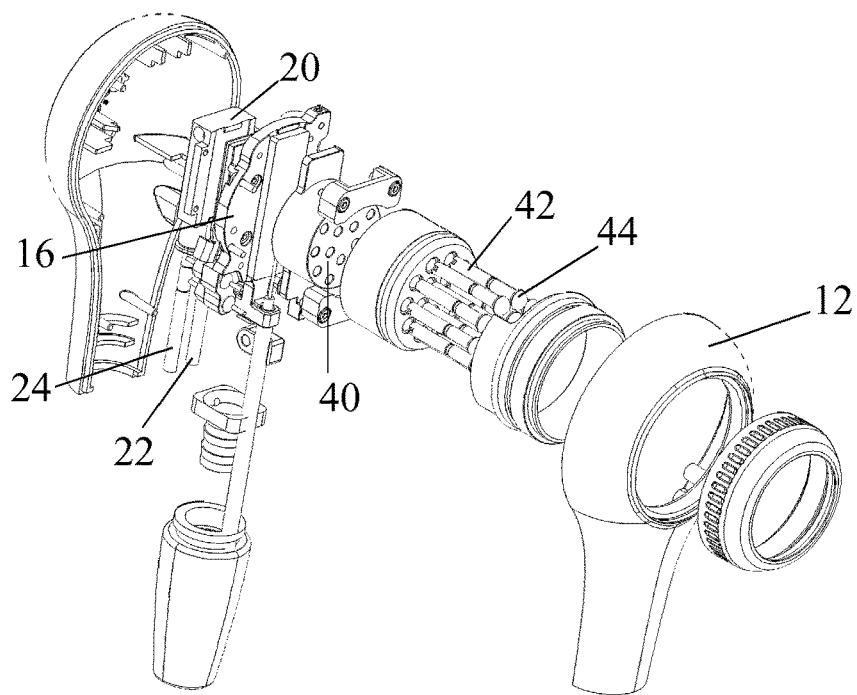
FIG. 8 is an exploded view of the applicator shown in FIGS. 4 to 7.

The electrode and its contact regions 14 are seen in FIGS. 6 and 7. FIG. 6 shows interior of the applicator 10 from the front after removal only of the outer shell, while in FIG. 7 several components have been removed to expose the electrode. The latter comprises a cylindrical base 40, made of an electrically conductive material, usually aluminium which is clamped to a plate 16. A plurality of electrically conductive pins 42, with rounded or flat tips, are screwed into the base 40 and their contact regions are covered with insulators 44. The adjustability of the individual pins 42 allows the contour of the envelope of the contact regions to be made either flat or rounded.

Figure 9:
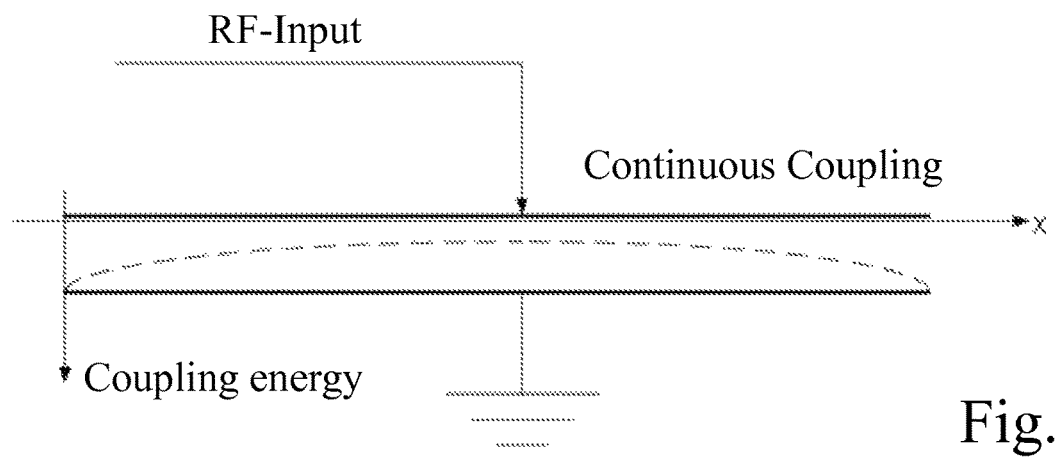
FIG. 9 is a schematic representation of the coupling energy when using a large continuous contact region to apply RF energy to biological tissue.
Figure 10:
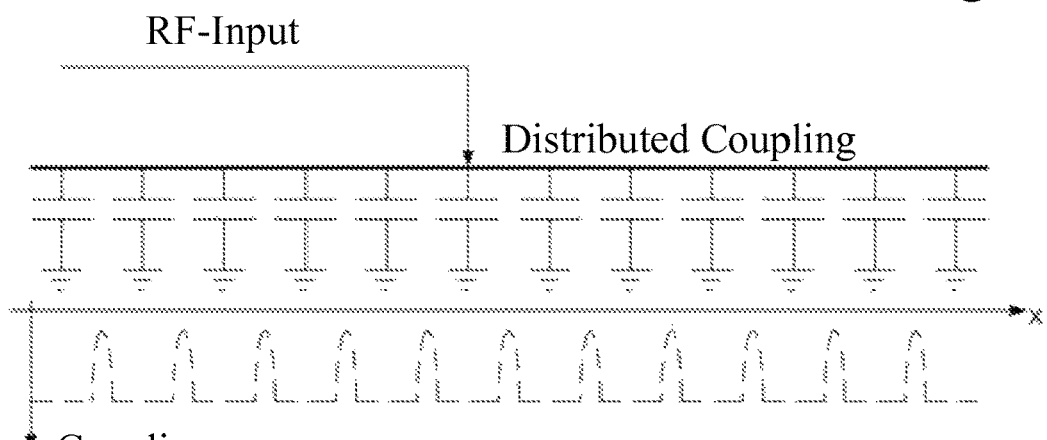
FIG. 10 is a schematic representation of the coupling energy when using a distributed contact region made up of several small areas, as taught by the present invention.

FIG. 9 shows the RF coupling in the case of an electrode with a large single contact region, corresponding to the situation shown in FIG. 3. The energy coupling is seen to be at maximum near the periphery of the electrode and a minimum on the axis. The effect achieved by the electrode of the FIGS. 4 to 8 on the other hand is represented in FIG. 10. In this case, each contact region achieves uniform heating beneath it with a lesser degree of heating between the individual contact region as a result of constructive interference between the waves emitted in phase from different pins.

Close spacing of the pins allows the cooler regions in the biological tissue between the pin contact regions to be minimised and it is also possible to place a motor in the applicator to rotate the electrode in order to avoid cold spots within the area of the electrode. In this way, the invention allows the use of high frequency RF energy while still being able to treat larger areas. Furthermore, as the energy is distributed over a larger area than can be achieved using a single contact region, it is possible to use the RF source on a higher power setting.

The invention claimed is:

1. An electrode for use in a system for heating biological tissue via RF energy, the electrode comprising a plurality of electrically conductive pins projecting from, and in electrical contact with, an electrically conductive common base,
   wherein the base is directly connected to a source of RF energy operable at a frequency in the range 30 MHz to 100 MHz and the spaced ends of the pins remote from the base have rounded or flat contact regions for capacitively coupling RF energy from the source into the biological tissue,
   wherein, when the electrode is being operated to treat the biological tissue, the contact regions of the pins contact the biological tissue and capacitively couple RF energy into the biological tissue, wherein a ground electrode is absent, permitting homogeneous application of RF energy;

wherein each contact region has a diameter of 3 cm or less, and wherein the system is non-invasive.

2. An electrode as claimed in claim 1, wherein at least the contact regions of the pins are covered with an electrically insulating material.

3. An electrode as claimed in claim 1, wherein the electrode is mounted in an applicator incorporating a motor for rotating the electrode.

4. An electrode as claimed in claim 1, wherein the electrode is mounted within an applicator that further comprises a cooling circuit for cooling the electrode.

5. An electrode as claimed in claim 1, wherein the electrode is mounted within an applicator that further houses components of a circuit supplying RF energy to the electrode.

6. An electrode as claimed in claim 1, wherein the RF energy source is capable of generating RF energy with a power in the range of 100 to 400 Watts.

7. An electrode as claimed in claim 1, wherein the RF energy source is capable of generating RF energy with a power in the range of 200 to 400 Watts.

8. An electrode as claimed in claim 1, wherein the contact regions as a group have a diameter of 4 cm to 6 cm.

9. An electrode as claimed in claim 1, wherein the contact regions are rounded.

10. An electrode for use in a system for heating biological tissue via RF energy, the electrode comprising a plurality of electrically conductive pins projecting from, and in electrical contact with, an electrically conductive common base, wherein the base is directly connected to a source of RF energy operable at a frequency in the range 30 MHz to 100 MHz and the spaced ends of the pins remote from the base have rounded or flat contact regions for capacitively coupling RF energy from the source into the biological tissue, wherein, when positioned for treatment of the biological tissue, each of the contact regions of the pins is in contact with the biological tissue, wherein a ground electrode is absent, permitting homogeneous application of RF energy, wherein each contact region is sized to achieve uniform dielectric heating in the biological tissue beneath the contact region at a predetermined frequency of applied RF energy and wherein the heating produced by the contact regions as a group is substantially equivalent to heating by a single electrode of equivalent area, and wherein the system is non-invasive.

11. An electrode as claimed in claim 10 wherein the area covered by the contact regions has a diameter of 4 cm to 6 cm.

12. An electrode as claimed in claim 10, wherein the RF energy source is capable of generating RF energy with a power in the range of 200 to 400 Watts.

13. An electrode as claimed in claim 10, wherein each contact region has a diameter of 1 cm or less.

14. An electrode as claimed in claim 11, wherein each contact region has a diameter of 3-4 cm.

15. An electrode as claimed in claim 11, wherein each contact region has a radius of $$\sqrt{\left(\frac{2\rho}{\omega\mu}\right)},$$

where $\rho$ is a resistivity of contact region material, $\mu$ is a permeability of the contact region material, and $\omega$ is a predetermined operating frequency between 30 MHz and 100 MHz.

* * * * *